United States Patent
Jones et al.

(10) Patent No.: US 7,750,192 B2
(45) Date of Patent: Jul. 6, 2010

(54) PURIFICATION OF FLUOROMETHYL 1,1,1,3,3,3-HEXAFLUOROISOPROPYL ETHER (SEVOFLURANE)

(75) Inventors: Barry Jones, Martinez, GA (US); Joel Swinson, Evans, GA (US)

(73) Assignee: Halocarbon Products Corporation, River Edge, NJ (US)

(*) Notice: Subject to any disclaimer, the term of this patent is extended or adjusted under 35 U.S.C. 154(b) by 278 days.

(21) Appl. No.: 11/997,435

(22) PCT Filed: Aug. 2, 2006

(86) PCT No.: PCT/US2006/030046

§ 371 (c)(1),
(2), (4) Date: Jan. 31, 2008

(87) PCT Pub. No.: WO2007/019161

PCT Pub. Date: Feb. 15, 2007

(65) Prior Publication Data

US 2008/0214875 A1      Sep. 4, 2008

Related U.S. Application Data

(60) Provisional application No. 60/705,408, filed on Aug. 4, 2005.

(51) Int. Cl.
  *C07C 41/34*  (2006.01)
(52) U.S. Cl. ...................................... 568/682; 568/683
(58) Field of Classification Search .................. None
  See application file for complete search history.

(56) References Cited

U.S. PATENT DOCUMENTS 4,250,334 A    2/1981    Coon et al.
5,969,193 A    10/1999   Terrell

*Primary Examiner*—Rosalynd Keys
(74) *Attorney, Agent, or Firm*—Norris McLaughlin & Marcus, P.A.

(57) ABSTRACT

Crude sevoflurane product comprising unacceptably high levels of HFIP can be purified by combining the crude sevoflurane product with sufficient water to produce a multiphase mixture, fractionally distilling the multiphase mixture, removing sevoflurane from the distilling multiphase mixture as an azeotrope with water, and separating substantially pure sevoflurane from the azeotrope.

17 Claims, No Drawings

PURIFICATION OF FLUOROMETHYL 1,1,1,3,3,3-HEXAFLUOROISOPROPYL ETHER (SEVOFLURANE)

BACKGROUND OF THE INVENTION

1. Field of the Invention

The present invention relates generally to the production of 1,1,1,3,3,3-hexafluoroisopropyl ether (sevoflurane), which is widely used around the world as an inhalation anesthetic.

2. Description of Related Art

There are several known methods for the production of sevoflurane, particularly by the reaction of formaldehyde (or a formaldehyde equivalent), hydrogen fluoride (HF), and hexafluoroisopropanol (HFIP). U.S. Pat. No. 4,250,334 describes a process in which HFIP is added to a mixture of a stoichiometric excess of paraformaldehyde and HF plus sufficient sulfuric acid to sequester most of the water formed in the reaction. WO 97/25303 describes a process for the production of sevoflurane in which essentially pure bis(fluoromethyl)ether (BFME) is allowed to react with HFIP and sulfuric acid. U.S. Pat. No. 6,469,219 describes a process in which HFIP and a formaldehyde equivalent are allowed to react with excess HF under distillative or extractive conditions in order to produce sevoflurane.

In all of these processes, unreacted HFIP may remain in the product mixture, as well as BFME, methyl hexafluoroisopropyl ether (MHFIP), polyethers containing the HFIP and formaldehyde moieties, and various other undesired species. These impurities must be removed from the crude sevoflurane product in order to obtain a pharmaceutically acceptable form of the material. Many of these impurities can be removed by distillation, but HFIP is difficult to separate from sevoflurane since they have similar boiling points and may distill as an azeotrope. Simple washing of the crude sevoflurane product with water has been found to be inefficient, time consuming, and costly.

WO 99/44978 describes a process for the removal of HFIP from sevoflurane by performing aqueous base washes of a crude sevoflurane product. This process requires meticulous control of the amount of base used in proportion to the amount of HFIP present, as well as careful temperature control in order to avoid the conversion of some of the sevoflurane to compound A, a highly toxic and undesired side product. Also, prolonged processing is required with repeated sampling and analysis, in order to ensure adequate removal of HFIP without forming too much compound A. Thus, this approach adds an unattractive amount of cost and complexity to the production process.

WO02/50005 and related US 2004/0124076 describe a process for purifying a crude sevoflurane product by contacting a crude composition of sevoflurane and HFIP with a modifier to decrease the vapor pressure of the ether and/or alcohol, preferably by decreasing the vapor pressure of HFIP. The ether and alcohol then may be separated by distillation. The modifier typically is an amine or some other group that is capable of bonding with HFIP, or at least donating electrons to the alcohol. The use of such a modifier adds cost and complexity to the production process since it must be completely removed from both the sevoflurane product, as well as the unreacted HFIP that is recycled back into the reaction phase. The modifier then must either be recycled or isolated for disposal. Odor issues are also of concern when amines or thiols are used as the modifier.

Addition of alkali metal salts to the distillation of sevoflurane is described in U.S. Pat. No. 5,684,211 as a method to suppress the decomposition, which forms Compound A. The patent does not speak to hexafluoroisopropanol, azeotropes of it or methods of its removal by distillation.

Middleton and Lindsey in the Journal of the American Chemical Society, 1964, 86: 4948-4952 have described azeotropes of fluorinated secondary alcohols such as hexafluoroisopropanol in which the normal boiling point is higher than the alcohol. Methods of breaking these azeotropes were also described, but applications of these azeotropes were not described.

Other proposed methods of sevoflurane synthesis, such as that described in U.S. Pat. No. 6,100,434, avoid this difficult sevoflurane/hexafluoroisopropanol separation by using more complicated synthetic strategies.

What is still needed is a distillative method for the efficient separation of sevoflurane and hexafluoroisopropanol.

BRIEF SUMMARY OF THE INVENTION

This and other objects were met with the present invention, which relates in a first embodiment to a process for obtaining substantially pure fluoromethyl 1,1,1,3,3,3-hexafluoroisopropyl ether (sevoflurane) from a crude sevoflurane product comprising sevoflurane and 1,1,1,3,3,3-hexafluoroisopropanol (HFIP), wherein the process comprises the following steps:
 a) providing the crude sevoflurane product;
 b) combining the crude sevoflurane product with sufficient water to produce a multiphase mixture;
 c) fractionally distilling the multiphase mixture;
 d) removing sevoflurane from the fractionally distilling multiphase mixture as an azeotrope with water; and
 e) separating substantially pure sevoflurane from the azeotrope.

The inventive purification method permits an improved process for preparing sevoflurane. Thus, the present invention relates in a second embodiment to a process for producing substantially pure fluoromethyl 1,1,1,3,3,3-hexafluoroisopropyl ether (sevoflurane), wherein the process comprises the following steps:
 a) reacting HFIP, formaldehyde and hydrogen fluoride (HF) to produce a first crude sevoflurane product comprising HFIP;
 b) obtaining a second crude sevoflurane product comprising HFIP from said first crude sevoflurane product;
 c) combining the second crude sevoflurane product with sufficient water to produce a multiphase mixture;
 d) fractionally distilling the multiphase mixture;
 e) removing sevoflurane from the fractionally distilling multiphase mixture as an azeotrope with water; and
 f) separating substantially pure sevoflurane from the azeotrope.

DETAILED DESCRIPTION OF THE INVENTION

The present invention provides an improved process for preparing sevoflurane substantially free of HFIP. The phrase "sevoflurane substantially free of HFIP," as used in the specification and in the appended issued claims means sevoflurane containing less than 20 ppm of HFIP. The phrase "substantially pure sevoflurane," as used in the specification and in the appended issued claims means sevoflurane which contains less than 100 ppm of total impurities, and less than 20 ppm of any individual impurity.

In the course of studies designed to meet the goal of developing a distillative method for the efficient separation of sevoflurane and HFIP, we unexpectedly discovered that sevoflurane may be distilled away from HFIP in high purity (<20 ppm HFIP in the overhead product) simply by adding enough water to a crude sevoflurane product to form a multiphase system that preferably persists throughout the distillative process. Most of the HFIP is extracted from the sevoflurane layer and into the aqueous layer, where it stays during the remainder of the distillation. The net result of the fractional distillation is that sevoflurane is taken overhead as a low-boiling azeotrope with water, substantially free of HFIP. The sevoflurane/water overhead product forms two layers which are then simply separated.

Specifically, it has been discovered that a crude sevoflurane product comprising unacceptably high levels of HFIP can be purified by combining the crude sevoflurane product with sufficient water to produce a multiphase mixture, fractionally distilling the multiphase mixture, and removing substantially pure sevoflurane from the fractionally distilling multiphase mixture.

The crude sevoflurane product comprising HFIP can be prepared in any manner, but is preferably produced by a process comprising reacting HFIP, formaldehyde and hydrogen fluoride (HF). Such a process is described in U.S. Pat. No. 6,469,219, the entire contents of which are hereby incorporated by reference. The term "formaldehyde," as used therein, and as used herein, means not only formaldehyde per se, but, also, any equivalent of formaldehyde, for example, formaldehyde polymers, such as trioxane, and paraformaldehyde.

In a preferred embodiment, the crude sevoflurane product is prepared by reacting HFIP, formaldehyde and a stoichiometric excess of HF. The reaction temperature is not critical, but the yields are substantially improved above 50° C. Preferably, the reaction is conducted under autogenous pressure of 30-40 psig ensuring temperatures of 45-75° C.

In the preferred embodiment, water is added to a crude sevoflurane product containing HFIP and other impurities in an amount sufficient to produce a multiphase mixture. How much water is added can be determined empirically, but the quantity is limited on the one hand by the necessity to maintain a multiphase system throughout the distillative process, while on the other hand maintaining process efficiency by minimizing the size of the equipment and time required to perform the process. Thus, a preferred embodiment of this invention would use 5-200% (volume) of water for the crude sevoflurane that is to be purified. A more preferred embodiment would use 20-75% of water for the crude sevoflurane that is to be purified.

Once the multiphase mixture is produced, this is then subjected to fractional distillation according to well known protocol. Again, fractional distillation is used in U.S. Pat. No. 6,469,219, the entire contents of which have already been incorporated herein by reference. The fractional distillation here can be conducted in an analogous manner, as a continuous process, or in a batchwise manner. The distillation may be performed at reduced, elevated, or ambient pressure.

In addition to producing crude sevoflurane, the reaction of HFIP, formaldehyde and HF may produce a number of well known impurities, among them bis(fluoromethyl)ether (BFME), methyl hexafluoroisopropyl ether (MHFIP), methyl 2,2,2-trifluoro-1-(trifluoromethyl)ethyl ether (SME), and polyethers containing the HFIP and formaldehyde moieties. In addition, the reacting mixture may also contain as yet unreacted starting materials, which can also be present as impurities in the crude sevoflurane product.

It has been discovered that the inventive process provides a simple and efficient way of purifying the crude sevoflurane product of these impurities. When water is added to the aforementioned crude sevoflurane product in sufficient amount to produce a multiphase mixture (which multiphase mixture preferably exists for the remainder of the process) and the heterogeneous mixture produced is then subjected to fractional distillation as described herein, impurities that boil at a temperature below that of sevoflurane ("low-boiling" impurities), such as BFME and SME, can be removed in a forecut, then substantially pure sevoflurane can be removed overhead in a heartcut, and impurities that boil at a temperature above that of sevoflurane ("high-boiling" impurities), such as HFIP, can be removed in an aftcut. In this preferred embodiment, it has been discovered that the high-boiling impurities remain in the distillation pot until >75% of the substantially pure sevoflurane has been removed overhead. As noted above, the sevoflurane isolated in this manner contains less than 100 ppm of total impurities, and less than 20 ppm of any individual impurity. Moreover, both the forecut and the aftcut can be recycled to the sevoflurane preparation step. Recovery of the aftcut preferably is effected simply by collecting more volatiles overhead until the pot temperature nears the boiling point of water.

The invention will now be described in greater detail with reference to the following non-limiting example:

EXAMPLE

The process is conducted in a vessel equipped with a fractional distillation column, a temperature-sensing device, condenser, gas outlet, liquid inlet and stirring bar. The distillation vessel is charged with a crude sevoflurane product comprising sevoflurane, HFIP, and small amounts of HF and other organic compounds. Sufficient water is added to form a multiphase mixture. The mixture is warmed, and from the column, a forecut is collected, which contains BFME and other low-boiling impurities and small amounts of sevoflurane product. After the forecut, a heartcut is collected, which contains sevoflurane product in high purity (>99.99%). The distillation vessel's temperature is raised and an aftcut is collected, which contains HFIP and other high-boiling impurities. The aftcut may be returned to the sevoflurane production process, with or without further purification.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A process for obtaining substantially pure fluoromethyl 1,1,1,3,3,3-hexafluoroisopropyl ether (sevoflurane) from a crude sevoflurane product comprising sevoflurane and 1,1,1,3,3,3-hexafluoroisopropanol (HFIP), said process comprising the following steps:
    a) providing said crude sevoflurane product;
    b) combining said crude sevoflurane product with sufficient water to produce a multiphase mixture;
    c) fractionally distilling the multiphase mixture;
    d) removing sevoflurane from the fractionally distilling multiphase mixture as an azeotrope with water; and
    e) separating substantially pure sevoflurane from the azeotrope.

2. The process according to claim 1, wherein said crude sevoflurane product is produced by a process comprising reacting HFIP, formaldehyde and hydrogen fluoride (HF).

3. The process according to claim 2, which comprises reacting HFIP, formaldehyde and a stoichiometric excess of HF.

4. The process according to claim 2, which comprises reacting HFIP, formaldehyde and HF in a reactor to produce a crude sevoflurane product, isolating a second crude sevoflurane product from said first crude sevoflurane product, and adding said sufficient water to said second crude sevoflurane product to produce said multiphase mixture.

5. The process according to claim 1, which is conducted at elevated pressure.

6. The process according to claim 1, which is conducted at reduced pressure.

7. The process according to claim 1, wherein the crude sevoflurane product additionally comprises at least one impurity selected from the group consisting of bis(fluoromethyl) ether (BFME), methyl hexafluoroisopropyl ether (MHFIP), methyl 2,2,2-trifluoro-1-(trifluoromethyl)ethyl ether (SME), and polyethers containing the HFIP and formaldehyde moieties.

8. The process according to claim 1, which comprises fractionally distilling the multiphase mixture and removing a forecut comprising at least one impurity having a boiling point lower than the boiling point of sevoflurane, and then removing a heartcut comprising substantially pure sevoflurane as an overhead product.

9. The process according to claim 8, which, after removing the heartcut comprising substantially pure sevoflurane, additionally comprises removing an aftcut comprising at least one impurity having a boiling point higher than the boiling point of sevoflurane.

10. A process for producing substantially pure fluoromethyl 1,1,1,3,3,3-hexafluoroisopropyl ether (sevoflurane), said process comprising the following steps:
    a) reacting HFIP, formaldehyde and hydrogen fluoride (HF) to produce a crude sevoflurane product comprising HFIP;
    b) obtaining a second crude sevoflurane product comprising HFIP from said first crude sevoflurane product;
    c) combining said second crude sevoflurane product with sufficient water to produce a multiphase mixture;
    d) fractionally distilling the multiphase mixture;
    e) removing sevoflurane from the fractionally distilling multiphase mixture as an azeotrope with water; and
    f) separating substantially pure sevoflurane from the azeotrope.

11. The process according to claim 10, which comprises reacting HFIP, formaldehyde and a stoichiometric excess of HF.

12. The process according to claim 10, which comprises reacting HFIP, formaldehyde and HF in a reactor to produce said crude sevoflurane product, isolating a second crude sevoflurane product, and adding said sufficient water to said second crude sevoflurane product to produce said multiphase mixture.

13. The process according to claim 10, which is conducted at elevated pressure.

14. The process according to claim 10, which is conducted at reduced pressure.

15. The process according to claim 10, wherein the crude sevoflurane product additionally comprises at least one impurity selected from the group consisting of bis(fluoromethyl) ether (BFME), methyl hexafluoroisopropyl ether (MHFIP), methyl 2,2,2-trifluoro-1-(trifluoromethyl)ethyl ether (SME), and polyethers containing the HFIP and formaldehyde moieties.

16. The process according to claim 10, which comprises fractionally distilling the multiphase mixture and removing a forecut comprising at least one impurity having a boiling point lower than the boiling point of sevoflurane, and then removing a heartcut comprising substantially pure sevoflurane as an overhead product.

17. The process according to claim 16, which, after removing the heartcut comprising substantially pure sevoflurane, additionally comprises removing an aftcut comprising at least one impurity having a boiling point higher than the boiling point of sevoflurane, and, optionally, recycling to step a) said at least one impurity having a boiling point higher than the boiling point of sevoflurane.

* * * * *